(12) United States Patent
Tao et al.

(10) Patent No.: US 7,594,893 B2
(45) Date of Patent: Sep. 29, 2009

(54) METHOD AND APPARATUS FOR CALCULATING BLOOD PRESSURE WITH SIGNAL TRANSFORMATION

(75) Inventors: Bo Tao, Nanshan (CN); Xu Zhang, Nanshan (CN); Jilun Ye, Nanshan (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 614 days.

(21) Appl. No.: 11/312,720

(22) Filed: Dec. 20, 2005

(65) Prior Publication Data

US 2007/0049834 A1 Mar. 1, 2007

(30) Foreign Application Priority Data

Aug. 31, 2005 (CN) .................. 2005 1 0036999

(51) Int. Cl.
*A61B 5/02* (2006.01)

(52) U.S. Cl. .................. 600/500; 600/485; 600/490

(58) Field of Classification Search .............. 600/506, 600/485, 494, 500, 495, 547
See application file for complete search history.

(56) References Cited

U.S. PATENT DOCUMENTS

| | | | | |
|---|---|---|---|---|
| 4,771,790 | A * | 9/1988 | Yamasawa et al. | 600/499 |
| 5,099,853 | A * | 3/1992 | Uemura et al. | 600/492 |
| 5,522,395 | A * | 6/1996 | Shirasaki et al. | 600/495 |
| 5,623,933 | A * | 4/1997 | Amano et al. | 600/500 |
| 5,730,137 | A * | 3/1998 | Amano et al. | 600/485 |
| 5,776,071 | A * | 7/1998 | Inukai et al. | 600/493 |
| 5,836,887 | A * | 11/1998 | Oka et al. | 600/494 |
| 5,961,467 | A * | 10/1999 | Shimazu et al. | 600/485 |
| 6,458,085 | B1 | 10/2002 | Wu et al. | |
| 6,748,262 | B2 * | 6/2004 | Harada et al. | 600/513 |
| 2005/0256385 | A1 * | 11/2005 | Diab et al. | 600/323 |
| 2007/0185429 | A1 * | 8/2007 | O'Mahony et al. | 604/4.01 |

FOREIGN PATENT DOCUMENTS

| | | |
|---|---|---|
| CN | 1274269 | 11/2000 |
| CN | 1513417 | 7/2004 |
| CN | 1608583 | 4/2005 |
| CN | 1608584 | 4/2005 |
| CN | 1642475 | 7/2005 |

* cited by examiner

*Primary Examiner*—Charles A Marmor, II
*Assistant Examiner*—Michael D'Angelo
(74) *Attorney, Agent, or Firm*—Kory D. Christensen; Stoel Rives LLP (57) ABSTRACT

A method and an apparatus for calculating blood pressure with signal transformation are provided, wherein said apparatus comprises: a pressure sensor, a pressure and pulse wave amplification circuit, an A/D converter, a microprocessor, a control circuit, an air pump and a valve component connected with the cuff gas circuit, a signal processing module and a ratio analysis module; and the method includes the steps of carrying out signal transformation of a time sequence of a sampled PW digital signal, calculating a maximum amplitude value and a corresponding frequency value based on the transformed signal, taking the maximum amplitude value as a amplitude value under the present pressure, carrying out continuously signal transformation of the time sequences of the PW digital signals at different pressure in order to constitute a PW amplitude-pressure curve and obtain an average pressure and a corresponding pulse rate from the PW amplitude-pressure curve, and finally calculating the systolic pressure and diastolic pressure with ratio method. With the method and apparatus according to the present invention, the measurement error can be reduced in case of the shiver, muscular fibrillation and the like of the human body being examined, and the measurement accuracy of blood pressure can be improved.

21 Claims, 5 Drawing Sheets

METHOD AND APPARATUS FOR CALCULATING BLOOD PRESSURE WITH SIGNAL TRANSFORMATION

FIELD OF THE INVENTION

This invention relates to a method and an apparatus for measuring blood pressure, and more particularly to the method and apparatus for improving the measurement accuracy with signal transformation of sampled signals.

DESCRIPTION OF THE RELATED ART

The conventional method for measuring blood pressure is using oscillation method, which includes steps of: obtaining a relationship curve between pulse pressures and pulse wave (PW) amplitudes by seeking PW amplitudes at various pressures; finding a pressure corresponding to a maximum PW amplitude as a mean pressure; multiplying the PW amplitude corresponding to the mean pressure by a systolic pressure amplitude coefficient to obtain a PW amplitude corresponding to the systolic pressure, calculating a pulse pressure according to the relationship curve and setting it as the systolic pressure; multiplying the PW amplitude corresponding to the mean pressure by a diastolic pressure amplitude coefficient to obtain a PW amplitude corresponding to the diastolic pressure, and then calculating a pulse pressure as the diastolic pressure according to the relationship curve. From the view of circuit functionality, it contains a power supply circuit, an inflation passage of a motor, valve and cuff, an amplifying and sampling portion for pressure signals, an A/D converter circuit, a logic control portion, a microprocessor data processing portion, a sequence port communication portion, and a hardware protection circuit.

Figure 1:
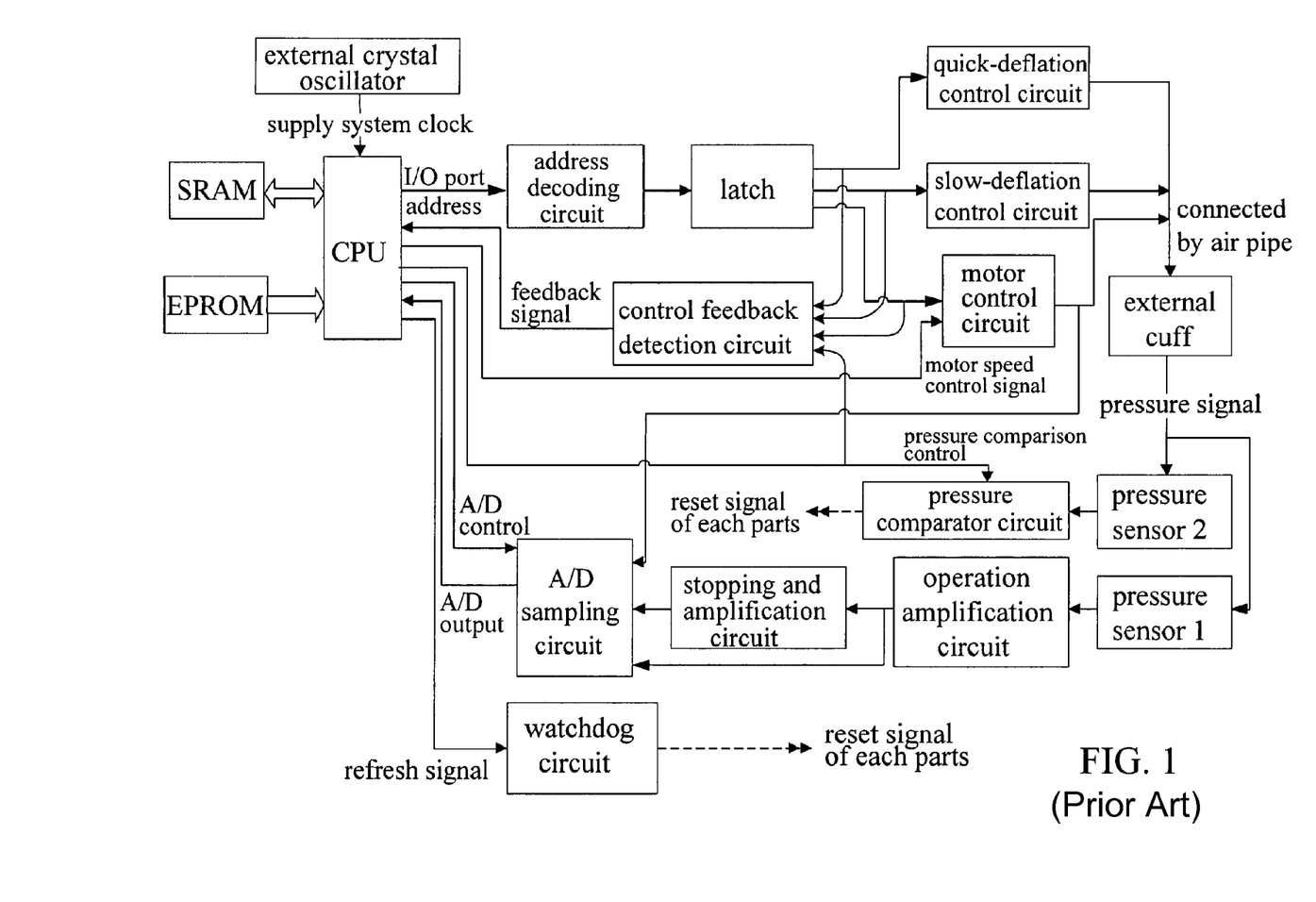
FIG. 1 is a principle block diagram of a hardware structure of a conventional blood pressure measurement apparatus.

The hardware structure of a conventional blood pressure measuring apparatus is shown in FIG. 1. The power supply circuit inputs a 12V direct current, and outputs 5 groups of voltage, digital +5V, digital +3.3V, analog +5V, analog +2.5V, analog +8V. The circuit provides a power supply for all hardware circuits. The functions of some electric components shown in FIG. 1 are described in brief as follows:

The inflation passage of the motor, valve and cuff is controlled by the logic control portion. The logic control portion can include a microcomputer, a quick-deflation valve control circuit, a slow-deflation valve control circuit, a motor control circuit and so on. The valve is firstly closed and the motor is energized to inflate the cuff to a predetermined pressure, then the inflation is stopped, and the valve is opened to release pressed air gradually.

Pressure sensors transform present pressure signals into electric signals, one way of which is outputted directly to an A/D converter circuit, so that a present pressure value is obtained by calculating, and the other way of which is outputted to the A/D converter circuit via a stopping and amplification circuit for filtering out the direct current pressure signals in order to obtain alternating current PW signals.

The amplified analog signals are converted into digital ones by the A/D converter circuit, and then outputted to the microprocessor to be processed. The microprocessor data processing portion will process and calculate the data after A/D converter circuit to obtain blood pressures and a pulse rate, and then output the blood pressures and pulse rate via the sequence port.

The hardware protection circuit comprises a pressure sensor and a pressure comparator circuit. If a pressure signal exceeds a certain amplitude, the input of the comparator circuit will exceed the threshold inversion, which results in the output of a low level to reset the system.

During the non-invasive blood pressure measurement, the cuff is inflated to a certain pressure and then deflated gradually. If the pressure achieved during such inflation is greater than the systolic pressure of the human body, it can be considered that the blood vessel is completely blocked, and no pulse throbs exist at the cuff. Then the deflation is started. When the cuff pressure is lower than the systolic pressure, the blood vessel has been partially opened up, and the pulse throbs will increase gradually with the decrease of the cuff pressure; however, due to the influence of the pulse throbs, the pressure of the cuff will have a fluctuation in a small range, namely, a oscillation signal is superimposed on the pressure signal, and this oscillation signal will also increase gradually with the decrease of the cuff pressure. When the cuff pressure decreases and reaches to a certain degree, the amplitude of the oscillation signal will begin to decrease instead, because the attenuation effect of the subcutaneous tissue of the human body to the pulse throbs is enhanced as the decrease of the cuff pressure. With the further decrease of the cuff pressure, the attenuation effect will become more evident, and the amplitude of the oscillation signal will be getting smaller.

During the measurement process, the cuff is winded around the arm of the human body being examined and inflated to a certain pressure, the human body being examined will inevitably feel compressed and shiver unconsciously; or the patient's condition of the human body being examined may result in the situations such as muscular fibrillation and the like. Under the situations, the baseline and amplitude of the PW will be affected. Therefore, the method of seeking wave crest and wave trough of the PW in the prior art is easy to be interfered by the above shiver, muscular fibrillation and the like. This may lead to apparent error for the PW amplitude and related calculation.

SUMMARY OF THE INVENTION

The technical problem to be solved by the present invention is to propose a method and an apparatus for measuring blood pressure, which can drastically decrease measurement errors due to the shiver, muscular fibrillation and the like of a human body being examined.

To solve the technical problems, the present invention provides a method for calculating blood pressure with signal transformation, wherein the method comprises the following steps of:

a. winding a cuff connected with a pressure sensor around an arm of a human body being examined, inflating the cuff to a certain pressure, and then deflating the cuff to a determined pressure;

b. maintaining the determined pressure for a predetermined time, continuously transforming both the pressure and a PW signal at the determined pressure into electric signals by the pressure sensor within the predetermined time, and transmitting the electric signals to an A/D converter circuit which converts the electric signals into a pressure value and a time sequence of a PW digital signal after the electric signals are amplified;

c. carrying out the signal transformation of the time sequence of the PW digital signal, calculating a maximum amplitude value and a frequency value corresponding to the maximum amplitude value at the determined pressure based on the transformed signal, taking the maximum amplitude value as an amplitude value at the determined pressure, taking the frequency value corresponding to the maximum amplitude value as a pulse rate value at the determined pressure, continuing to deflate the cuff to another determined pressure, and then returning to the step b till predetermined times;

d. constituting a PW amplitude value sequence and a pressure value sequence according to the amplitude value and the pressure value at each determined pressure, and then forming a PW amplitude-pressure curve according to the PW amplitude value sequence and the pressure value sequence;

e. calculating a mean pressure and a PW amplitude value P0 corresponding to the mean pressure based on the PW amplitude-pressure curve, respectively calculating PW amplitude values PS and PD which are corresponding to a systolic pressure and a diastolic pressure to be measured with ratio method, wherein PS=$\alpha$*P0, PD=$\beta$*P0, $\alpha$ and $\beta$ are a systolic pressure amplitude coefficient and a diastolic pressure amplitude coefficient respectively, and finally obtaining the systolic pressure and diastolic pressure based on the PW amplitude-pressure curve according to the PW amplitude values PS and PD.

According to the invention, the coefficients $\alpha$ and $\beta$ in the step e are empirical coefficients obtained from experiments, the value of $\alpha$ ranges from 0.2 to 0.9, and the value of $\beta$ ranges from 0.2 to 0.8.

According to the invention, the signal transformation of the time sequence of the PW digital signal refers to Chirp-Z transformation of the time sequence of the PW digital signal.

According to the invention, the predetermined times range from 6 to 10 times, and the predetermined time ranges from 3 to 10 seconds.

According to the invention, for the PW amplitude value sequence and pressure value sequence obtained at different determined pressures in the step d, a normalization, interpolation and weighted average processing is performed, and the PW amplitude-pressure curve is constituted according to the processed PW amplitude value sequence and pressure value sequence.

The present invention also provides an apparatus for calculating blood pressure with signal transformation, consisting of:

a data sampling unit including a cuff, a pressure sensor, a pressure amplification circuit, a PW amplification circuit and an A/D converter circuit, wherein the pressure sensor transforms a plurality of pressure and PW signals at different determined pressures into electric signals, which are transmitted to the A/D converter circuit and converted into pressure values and time sequences of PW digital signals after being amplified by the pressure amplification circuit and the PW amplification circuit respectively;

a primary control unit including a microprocessor with computer software and a control circuit, for controlling deflation time and deflation speed of the cuff according to the pressure signals and calculating blood pressure and pulse rate of a human body being examined by an arithmetic software;

an inflation and deflation unit including an air pump and a valve component which are connected with a cuff gas passage, for receiving control signals from the primary control unit to perform automatic inflation and deflation operation of the cuff, wherein the apparatus further comprises:

a signal processing module, for performing signal transformation of the time sequences of the PW digital signals at a plurality of determined pressures outputted by the A/D converter circuit, to obtain amplitude-frequency characteristics of data being analyzed and then get maximum amplitude values at the different determined pressures, which are closely related with the blood pressure of the human body being examined;

a ratio analysis module, for extracting the amplitude values at the plurality of determined pressures outputted by the signal processing module and the pressure values at the plurality of determined pressures outputted by the A/D converter circuit, to obtain a PW amplitude value sequence and a pressure value sequence so as to form a PW amplitude-pressure curve, seeking a maximum amplitude value during the whole measure process from the PW amplitude-pressure curve, and finally calculating and outputting the blood pressure and pulse rate of the human body being examined according to a certain ratio.

According to the invention, the signal transformation refers to Chirp-Z transformation of the time sequences of the PW digital signals.

According to the invention, the ratio analysis module further comprises a normalization block, an interpolation block and a weighted average block, for carrying out a normalization, interpolation and weighted average processing of the PW amplitude value sequence and the pressure value sequence, and then constituting the PW amplitude-pressure curve according to the processed PW amplitude value sequence and pressure value sequence.

According to the invention, the apparatus further includes an auxiliary functional module bidirectionally connected with the microcomputer, for resetting system, detecting leakage and calibrating pressure.

Compared with the prior art, the method and apparatus with signal transformation according to the present invention has the advantages as follow: by calculating the PW amplitude with the method of signal transformation, the anti-interference capability is improved and the measurement accuracy of blood pressure can be effectively improved in case of the shiver, muscular fibrillation and the like of the human being examined.

DETAILED DESCRIPTION OF THE PREFERRED EMBODIMENTS

The apparatus and method according to the present invention will be described in detail thereafter with reference to the accompanying drawings and embodiments shown in the drawings.

Figure 2:
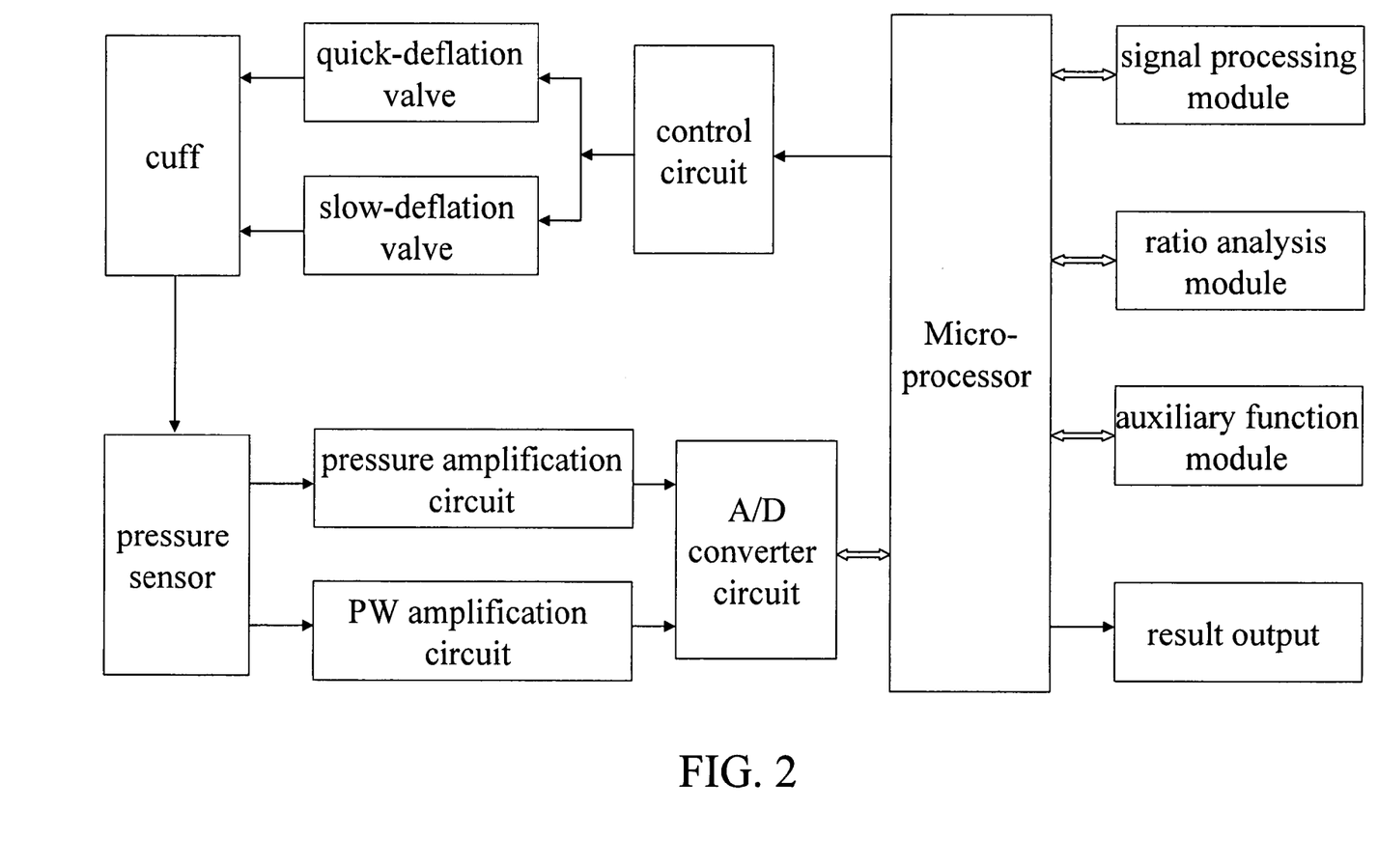
FIG. 2 is a principle block diagram of the apparatus for calculating blood pressure with signal transformation according to the present invention.

Since the difference between the apparatus according to the invention and the prior art lies in the algorithm module for processing the sampled PW, and the hardware portion of the apparatus is basically similar with the prior art, thus the description of the hardware portion which is identical with the apparatus in prior art will be simplified. As shown in FIG. 2, the apparatus for calculating the blood pressure with signal transformation according to the invention consists of:

a data sampling unit including a cuff, a pressure sensor, a pressure amplification circuit, a PW amplification circuit and an A/D converter circuit, wherein the pressure sensor transforms a present pressure and a PW signal of a human body being examined into electric signals, which are transmitted respectively to the A/D converter circuit and be converted into a pressure value and a time sequence of a PW digital signal after being amplified by the pressure amplification circuit and the PW amplification circuit;

a primary control unit including microprocessor with a computer software and a control circuit, for setting time and speed of deflation of the cuff according to the measurement requirements or controlling time and speed of deflation of the cuff according to the present pressure signal, and calculating blood pressure and pulse rate of a human body being examined by an algorithm software;

an inflation and deflation unit including an air pump and valve component connected with a cuff gas circuit, for receiving control signals from the primary control unit to perform automatic inflation and deflation operation of the cuff, wherein the valve component may comprise a quick-deflation valve and a slow-deflation valve;

an auxiliary functional module used for system reset, leakage detection and pressure calibration and the like; the difference between the apparatus according to the present invention and the prior art further lies in that the apparatus further includes:

a signal processing module, for signal transformation of the time sequence of the PW digital signal at a plurality of determined pressures outputted by the A/D converter, to obtain amplitude-frequency characteristics of data being analyzed and further get a maximum PW amplitude value at each determined pressure, which is closely related with the blood pressure of the human body; and Chirp-Z transformation is employed in the embodiment of the present invention, and transformation in other forms can also be used;

a ratio analysis module, for extracting the maximum PW amplitudes at the plurality of determined pressure outputted by the signal processing module and the pressures of the plurality of determined pressure outputted by the A/D converter to obtain a PW amplitude sequence and a pressure sequence, so that a relationship curve between PW amplitude and pressure can be formed; based on the relationship curve, a maximum amplitude value during the whole measurement process can be found, and then based on a ratio defined by the system, the blood pressure and pulse rate of the human body being examined can be calculated and output;

and the ratio analysis module further comprises a normalization block, an interpolation block and a weighted average block, for carrying out a normalization, interpolation and weighted average processing of the PW amplitude value sequence and the pressure value sequence, and then constituting the PW amplitude-pressure curve according to the processed PW amplitude value sequence and pressure value sequence, finally calculating and outputting the blood pressure and pulse rate of the human body being examined according to a certain ratio.

A preferred embodiment of the method for calculating blood pressure with signal transformation, in which the apparatus according to the present invention is the hardware basis, will be described in more detail thereafter, wherein said method comprises following steps.

Step a is winding a cuff connected with a pressure sensor around an arm of the human body being examined, inflating the cuff to a certain pressure, and then opening a valve to deflate the cuff to a determined pressure.

Step b is maintaining the determined pressure for predetermined time (i.e. timing interruption), continuously transforming both the pressure (its pressure unit is mmHg) and a PW signal into electric signals at the determined pressure by the pressure sensor within the predetermined time (for example, 3 seconds in this embodiment), and transmitting the electric signals to an A/D converter which converts the electric signals into a pressure value and a time sequence of a PW digital signal after the electric signals are amplified, namely pre-processing the sampled data.

Step c is carrying out the signal transformation of the time sequence of the PW digital signal. Since the deflation of the cuff is just finished and the wave form is not stable, 100 data sampled just during the initial stage is discarded. The subsequent 256 sampled data are selected to perform Chirp-Z transformation, and DFT (i.e. all the sampling values in an equal interval along a unit circle for Z transformation) of the finite sequence is calculated by means of FFT algorithm. However, in many circumstances, it is not necessary to calculate all the frequency spectrum values, but only to carry out a more intensive analysis on the signal frequency spectrum with a certain frequency band. Moreover, sampling is not necessary to be limited to the points along a unit circle, but needs to figure out the sampling values in an interval with an equal angle along a certain spiral curve. The Chirp-Z transformation is an algorithm which calculates the spiral curve sampling quickly with FFT algorithm, and the detailed algorithm is as follows.

Input N sampling values: $x[n]$ $n=0, 1, \ldots, N-1$

Sampling points in the spiral curve: $Z_k = AW^{-k}$ $K=0, 1, \ldots, M-1$ where $A = A_0 e^{j\theta_0}$ $W = W_0 e^{j\phi_0}$ A determines a starting angle, W determines a trend of the spiral curve, j is a complex number, $A_0$ indicates the initial radius of the spiral curve, $W_0$ indicates a rotational angle of the spiral curve, $\theta_0$ indicates a initial angle of the spiral curve, and $\phi_0$ indicates an interval angle along the spiral curve.

(1) Select the number of points L for FFT, which satisfies, $L \geq N+M-1$ and $L = 2^v$ where v is positive integer.

In a practical operation, N=M=256 points.

(2) Intercept one section h(n)

$h(n) = W^{n^2/2}$ $-(L-M) \leq n \leq M-1$ (3) Form a principal value sequence $\bar{h}(n)$ by h(n)

$$\bar{h}(n) = \begin{cases} h(n) = W^{-n^2/2} & 0 \leq n \leq M-1 \\ h(n-L) = W^{-(n-L)^2/2} & M \leq n \leq L-1 \end{cases}$$

(4) Calculate $H(k) = FFT[\bar{h}(n)]$ (5) Perform weighting and zero-padding to x(n)

$$g(n) = \begin{cases} x(n) \cdot A^{-n} W^{-n^2/2} & 0 \leq n \leq N-1 \\ 0 & N \leq n \leq L-1 \end{cases}$$

(6) Calculate $G(k) = FFT[g(n)]$ (7) Calculate $Y(k) = H(k)G(k)$ (8) Calculate y(n)=IFFT[Y(k)]

(9) Calculate $X(Z_k)=W^{n^2/2} \cdot y(n)$  $0 \leq n \leq M-1$

Figure 4:
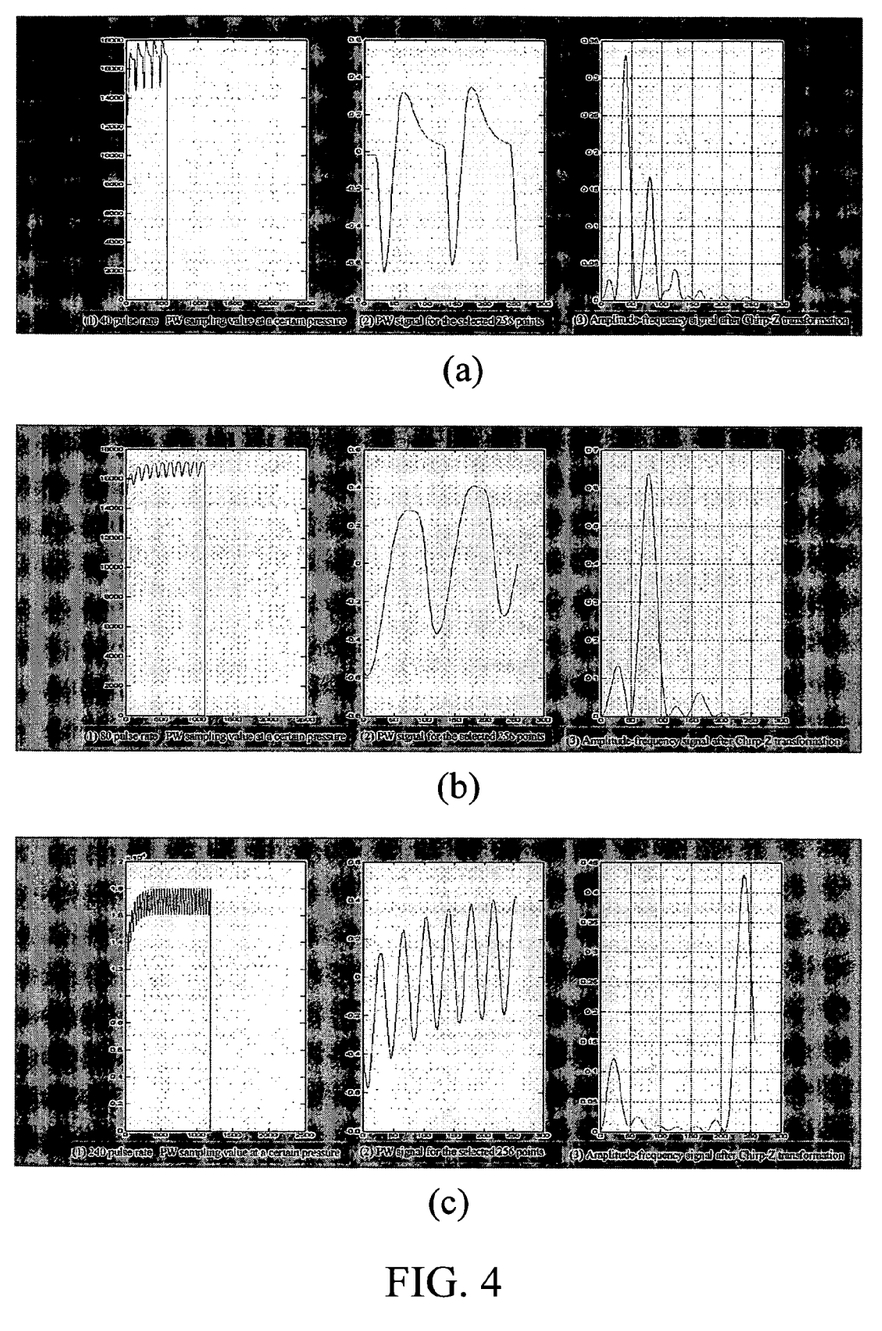
FIG. 4 are the schematic diagrams for Chirp-Z transformation of PW signals at various pulse rates, in which (a) indicates a case for pulse rate of 40 BPM, (b) indicates a case for pulse rate of 80 BPM, and (c) indicates a case for pulse rate of 240 BPM.

By carrying out Chirp-Z transformation of the above N sampling points, complex numbers $X(Z_k)$ of M points are obtained, wherein k=0, 1, ..., M−1, and the modulus of the complex numbers of the M points represent the signal amplitude value sequence within a certain frequency spectrum range. Therefore, by performing Chirp-Z transformation of 256 PW signal sampling values, a sequence of a PW digital signal within a corresponding frequency range is obtained, and the maximum PW amplitude value at the present pressure can be calculated based on this sequence of the PW digital signal, as shown in FIG. 4. The right side of FIG. 4 is the PW amplitude-frequency curve, and FIGS. 4(a), 4(b) and 4(c) each contains a evident main crest which is the maximum PW amplitude, and the frequency value to which the maximum PW amplitude corresponds is consistent with the original datum of the left side of FIG. 4; The PW amplitude-frequency curves in the right side also contain several secondary crests which are markedly smaller than the maximum PW amplitude and result from interference signals. In this invention, only the maximum PW amplitude and its corresponding frequency which bear physical meanings are analyzed, and the secondary crests will be ignored, so that the influence of interference signals on the measurement results is eliminated.

The maximum amplitude value and its corresponding frequency value are obtained with signal transformation, and the maximum amplitude value and the frequency value to which the maximum amplitude corresponds are calculated. The maximum amplitude value is regarded as an amplitude value at the present pressure and the frequency value to which the maximum amplitude corresponds is regarded as a pulse rate value at the present pressure. Continue to deflate the cuff to a next determined pressure (decrease to a next pressure step), and then return to step b) till predetermined times.

Step d is performing steps b and c repeatedly for predetermined times. In the embodiment, the predetermined times equals to 8 times, namely, the PW amplitude value sequence and pressure value sequence are constituted according to 8 amplitude values and 8 pressure values sampled at different determined pressures. Then perform a normalization, interpolation, and weighted average process for the two kinds of datum sequences, and constitute a PW amplitude-pressure curve according to the processed datum sequences.

Step e is calculating a mean pressure Mean and its corresponding PW amplitude value P0 based on the PW amplitude-pressure curve, respectively calculating PW amplitude values PS and PD which are corresponding to a systolic pressure SYS and a diastolic pressure DIA to be measured with ratio method, wherein PS=α*P0, PD=β*P0, and finally obtaining the systolic pressure and diastolic pressure with the PW amplitude-pressure curve according to the PW amplitude values PS and PD.

Figure 3:
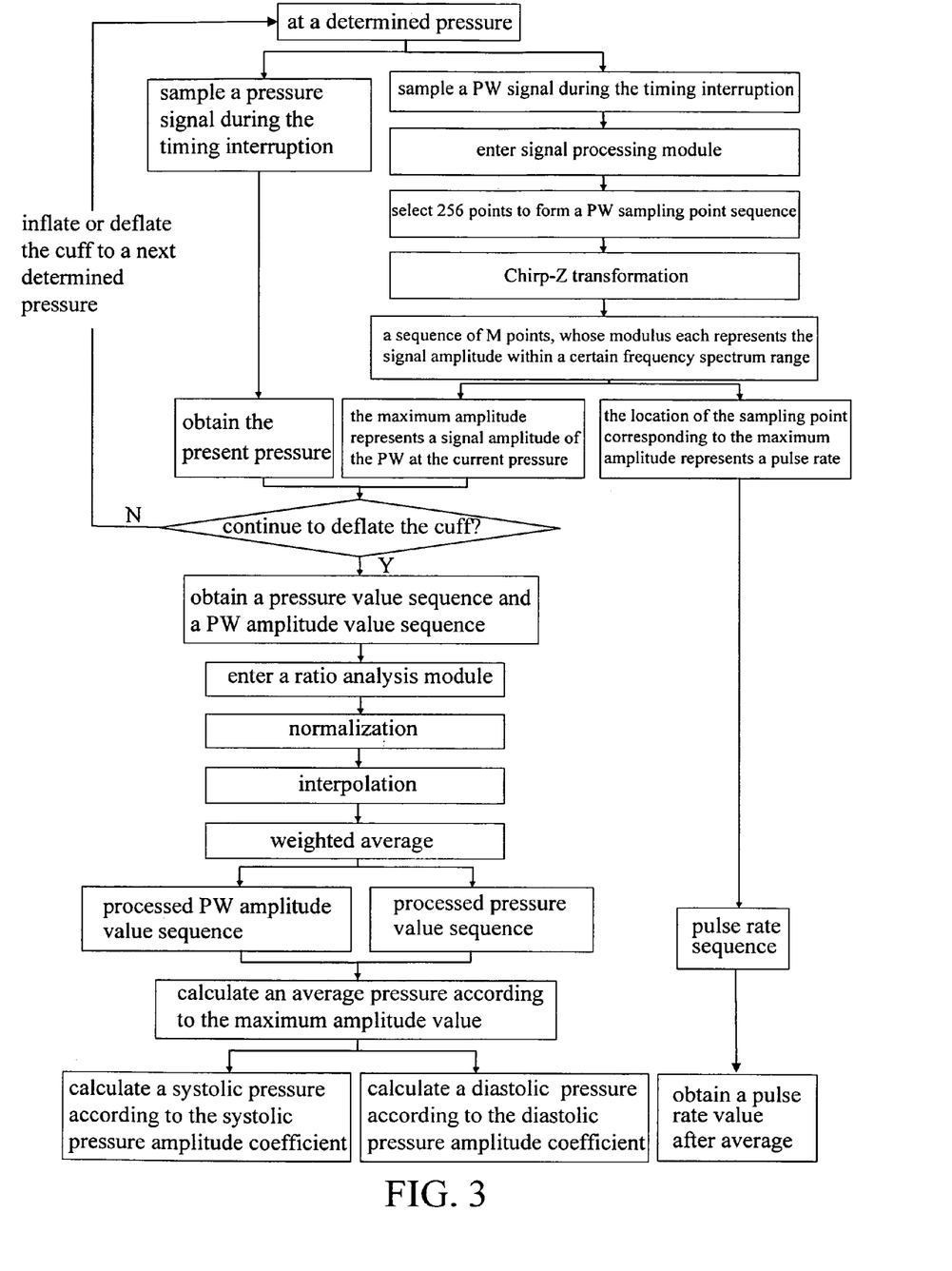
FIG. 3 is an algorithm flow chart of the signal processing module and ratio analysis module in FIG. 2.

The measurement and calculation flow chart for the above steps a to c is shown in FIG. 3.

The ratio method is based upon the following theory: when the cuff pressure equals to the diastolic pressure or systolic pressure, the ratio of corresponding PW amplitude to the maximum PW amplitude is relatively invariable. Once the maximum wave amplitude is confirmed, with the determined ratio, the PW amplitude to which the diastolic pressure or systolic pressure corresponds can be found, and thereby the pressure value of the corresponding diastolic pressure or systolic pressure can be obtained. In the method of the present invention, the determination of the ratio value is of vital importance. In general, the ratio depends on the characteristics of the apparatus and is an empirical coefficient obtained from large numbers of experiments. In this embodiment, the value of α ranges from 0.2 to 0.9, and the value of β ranges from 0.2 to 0.8.

Figure 5:
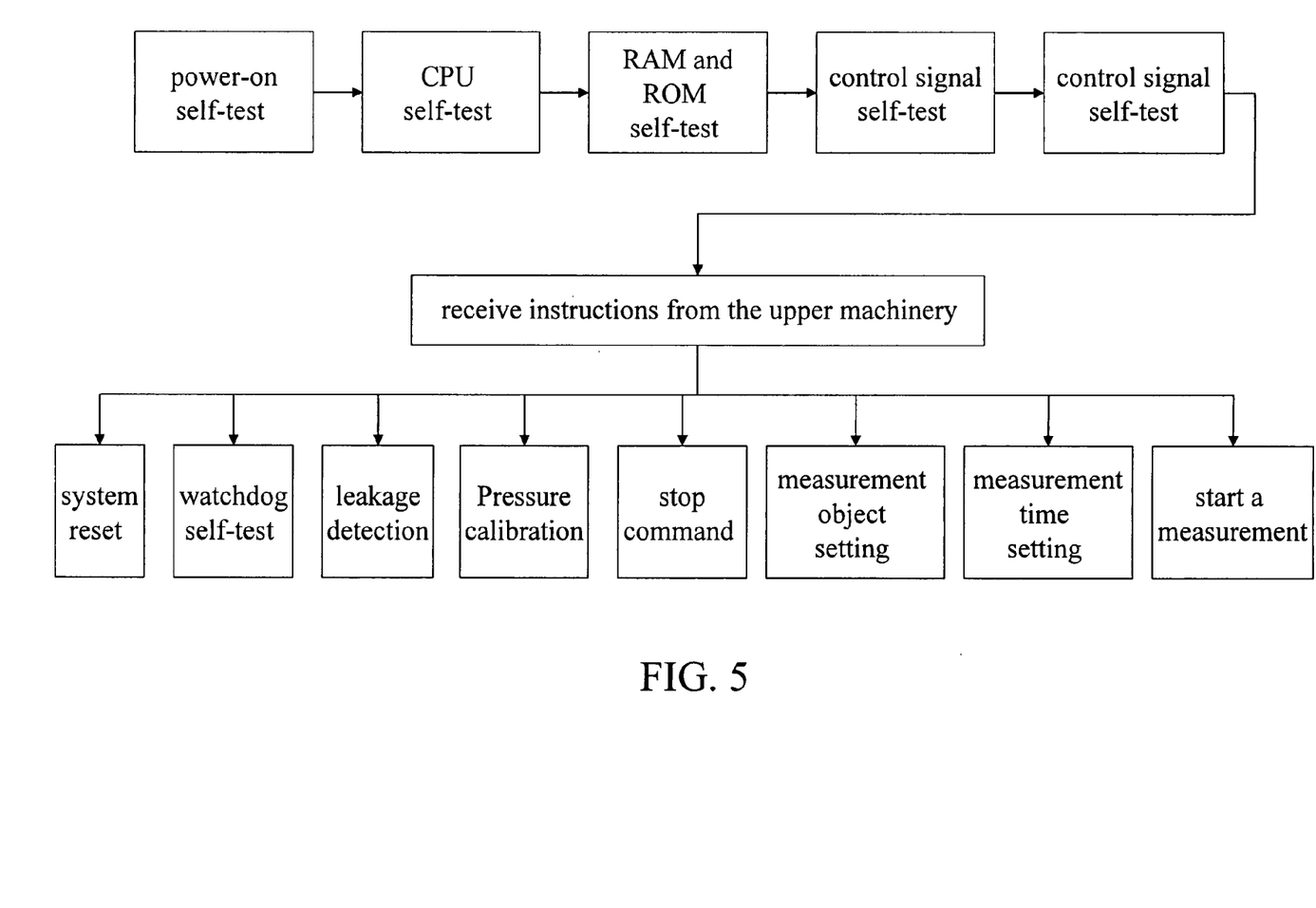
FIG. 5 is a flow chart of the system.

FIG. 5 is a flow chart of the apparatus according to the present invention, which is described in brief as follows:

(1) once being energized, carrying out the initialization of the hardware, system self-test and variable initialization, and then entering the primary program;

(2) setting timing interruption, and sampling pressure signals and PW signals during the timing interruption;

(3) receiving an instruction from the upper machinery so as to start a measurement, inflating the cuff to a certain pressure, then deflating the cuff to a determined pressure, and maintaining the determined pressure for a period of time (3 seconds), subsequently initiating the signal processing module and ratio analysis module, seeking the PW signal amplitude value at the pressure by calculation, then deflating the cuff again to reduce by a pressure step, i.e. at another determined pressure, initiating again the signal processing module and ratio analysis module, and then seeking the PW signal amplitude value at the pressure by calculation;

(4) by calculating the sampling data for 8 pressure steps (8 determined pressure), obtaining a PW amplitude-pressure curve, and calculating the average pressure, systolic pressure and diastolic pressure based on the PW amplitude-pressure curve;

(5) performing other auxiliary functions, such as leakage detection, pressure calibration and the like.

It has been proved by the tests in the laboratory, for a normal situation in which the pulse rate of the simulator is set at 40 BPM, 80 BPM, and 240 BPM and the blood pressure is 120/90/80 mmHg, the calculation results of the signal transformation algorithm are in accordance with those of the conventional algorithm. By using BIO-TECK simulator and simulating the case for 10 level of muscular fibrillation, which means approximately 10 times for the muscular fibrillation of a human body, the algorithm of signal transformation shows better results. The measurement results of the two algorithms are compared in the following table:

| Simulator setting | Calculation results of the signal transformation algorithm | Calculation results of the conventional algorithm | Comparison results |
|---|---|---|---|
| Cufflink simulator 120/90/80 40 BPM 100% gain | 121/92/82 40 BPM | 122/92/82 40 BPM | The results from the two algorithms coincide with each other |
| Cufflink simulator 120/90/80 80 BPM 100% gain | 120/90/83 80 BPM | 118/90/82 80 BPM | The results from the two algorithms coincide with each other |
| Cufflink simulator 120/90/80 240 BPM 100% gain | 122/92/82 238 BPM | 122/92/83 238 BPM | The results from the two algorithms coincide with each other |
| BIO-TEK simulator muscular fibrillation 10 level 120/93/80 80 BPM | 120/94/83 82 BPM | 130/99/85 82 BPM | The results from the signal transformation algorithm is closer to the simulator results |

What is claimed is:

1. A method for calculating blood pressure, comprising:
   acquiring a plurality of frequency domain pulse wave (PW) maximum amplitude values and associated pressure measurements from respective frequency domain representations of time domain PW pressure signals obtained at different respective measurement pressures, wherein acquiring a PW maximum amplitude and associated pressure measurement comprises:
   setting a pressure measurement device to a determined measurement pressure,
   receiving a pressure signal and a set of PW pressure signals from the pressure measurement device, wherein the set of PW pressure signals are received over a predetermined time period,
   constructing a PW time sequence comprising the set of PW pressure signals,
   calculating a frequency domain representation of the PW time sequence, and
   identifying a PW maximum amplitude value and PW frequency value in the frequency domain representation of the PW time sequence; and
   calculating a blood pressure value using the plurality of frequency domain PW maximum amplitude values and associated pressure values.

2. The method of claim 1, wherein the frequency domain PW maximum amplitude value is identified as the maximum amplitude value of the frequency domain representation of the PW time sequence.

3. The method of claim 2, wherein identifying the frequency domain PW frequency value comprises identifying the frequency of the PW maximum amplitude value in the frequency domain representation of the PW time sequence.

4. The method of claim 1, wherein the blood pressure value comprises a systolic blood pressure value (PS) and a diastolic blood pressure value (PD), and wherein calculating the PS and PD comprises:
   constructing a PW curve comprising the plurality of frequency domain PW amplitude values sequence and associated pressure measurements;
   calculating a mean pressure and mean PW amplitude value (P0) using the PW curve; and
   calculating the PS and PD values using the P0 value.

5. The method of claim 4, wherein the PS value is calculated by scaling the P0 value by a constant $\alpha$, and wherein $\alpha$ ranges from 0.2 to 0.9, and wherein the PD value is calculated by scaling the P0 value by a constant $\beta$, and wherein $\beta$ ranges from 0.2 to 0.8.

6. The method of claim 4, wherein constructing the PW curve further comprises:
   normalizing the plurality of frequency domain PW amplitude values and associated pressure values;
   constructing the PW curve by interpolation and weighted average processing performed on the normalized PW amplitude values.

7. The method of claim 1, wherein the frequency domain representation is calculated using one of a Chirp-Z transformation, a Fourier transform, and a discrete Fourier transform.

8. The method of claim 1, wherein 6 to 10 frequency domain PW maximum amplitude values are acquired, and wherein each of the 6 to 10 frequency domain PW maximum amplitude values are acquired at a different measurement pressure.

9. The method of claim 1, wherein the predetermined time period is 3 to 10 seconds.

10. An apparatus for calculating a blood pressure, comprising:
    a pressure measurement device configured to acquire a plurality of sets of pulse wave (PW) pressure signals and associated pressure measurements, wherein each set of PW pressure signals and associated pressure measurements are acquired at different measurement pressures and for a predetermined time period;
    a signal processing module configured to calculate a PW time sequence for each of the plurality of sets of PW pressure signals, to transform each of the PW time sequences into a respective frequency domain representation, and to identify within each frequency domain representation a frequency domain PW maximum amplitude value; and
    a ratio analysis module configured to calculate a blood pressure value using the plurality of frequency domain PW maximum amplitude values and associated pressure values.

11. The apparatus of claim 10, wherein the ratio analysis module is configured to construct a PW curve comprising the PW maximum amplitude values and associated pressure measurements and to determine a mean PW amplitude value (P0) therefrom, and wherein the ratio analysis module is configured to calculate PS and PD values using the P0 value.

12. The apparatus of claim 11, wherein the ratio analysis module is configured to calculate the PS value by scaling the P0 value by a constant value $\alpha$, and wherein $\alpha$ ranges from 0.2 to 0.9.

13. The apparatus of claim 11, wherein the ratio analysis module is configured to calculate the PD value by scaling the P0 value by a constant value $\beta$, and wherein $\beta$ ranges from 0.2 to 0.8.

14. The apparatus of claim 11, wherein the ratio analysis module is configured to normalize the plurality of PW maximum amplitude values, and wherein to construct the PW curve, the ratio analysis module is configured to process the normalized PW maximum amplitude values using interpolation and weighted averaging.

15. The apparatus of claim 10, wherein the signal processing module is configured to calculate the frequency domain representation of each of the PW time sequences using a Chirp-Z transformation.

16. The apparatus of claim 10, wherein the signal processing module is configured to calculate the frequency domain representation of each of the PW time sequences using a Fourier transform.

17. The apparatus of claim 10, wherein the signal processing module is configured to calculate the frequency domain representation of each of the PW time sequences using a discrete Fourier transform.

18. The apparatus of claim 17, wherein the measurement device comprises a control unit to control the measurement pressure of the measurement device.

19. The apparatus of claim 10, wherein the measurement device is configured to acquire 6 to 10 sets of PW pressure signals and associated pressure measurements.

20. The apparatus of claim 10, wherein the measurement device comprises an air pump and valve, and wherein the control unit controls the measurement pressure of the measurement device using the air pump and valve.

21. The apparatus of claim 10, wherein the measurement device comprises an A/D converter to convert pressure measurements acquired by the measurement device into digital signals.

* * * * *

UNITED STATES PATENT AND TRADEMARK OFFICE
CERTIFICATE OF CORRECTION

PATENT NO.       : 7,594,893 B2                              Page 1 of 1
APPLICATION NO.  : 11/312720
DATED            : September 29, 2009
INVENTOR(S)      : Tao et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 815 days.

Signed and Sealed this

Twenty-eighth Day of September, 2010

David J. Kappos
*Director of the United States Patent and Trademark Office*